United States Patent [19]
Ballard

[11] Patent Number: 5,458,486
[45] Date of Patent: Oct. 17, 1995

[54] DENTAL MIRROR APPARATUS

[76] Inventor: Stephen L. Ballard, 4125 Norwich Pl., Evansville, Ind. 47711

[21] Appl. No.: 177,758

[22] Filed: Jan. 4, 1994

Related U.S. Application Data

[63] Continuation-in-part of Ser. No. 852,966, Mar. 17, 1992, abandoned.

[51] Int. Cl.[6] ............................................. A61B 1/24
[52] U.S. Cl. ......................................... 433/30; 600/247
[58] Field of Search .............................. 433/30, 31, 163; 128/21, 22; 359/882; 362/138, 139

[56] References Cited

U.S. PATENT DOCUMENTS

| | | | |
|---|---|---|---|
| 159,836 | 2/1875 | Osborn | 433/30 |
| 224,663 | 2/1880 | Donaldson | 433/30 |
| 520,357 | 5/1894 | Hand . | |
| 606,456 | 6/1898 | Harnden | 433/30 |
| 849,209 | 4/1907 | Crawford | 362/139 |
| 1,079,414 | 11/1913 | Jirka | 433/30 |
| 1,220,252 | 3/1917 | Matthews | 362/139 |
| 1,387,770 | 8/1921 | Dolbey | 362/138 |
| 1,397,090 | 11/1921 | Dimas | 433/30 |
| 1,589,576 | 6/1926 | Thompson | 362/138 |
| 1,656,754 | 1/1928 | Norris | 362/139 |
| 2,055,188 | 9/1936 | Wappler et al. | 433/30 X |
| 3,352,305 | 11/1967 | Freedman | 433/31 X |
| 4,354,835 | 10/1982 | Lewis | 433/30 |
| 4,938,579 | 7/1990 | Kempf | 359/882 |
| 5,230,622 | 7/1993 | Brossoit | 433/30 X |
| 5,269,683 | 12/1993 | Hickok et al. | 433/30 |

FOREIGN PATENT DOCUMENTS

| | | | |
|---|---|---|---|
| 37662 | 7/1927 | Denmark | 433/30 |
| 836701 | 4/1952 | Germany | 433/30 |

*Primary Examiner*—Nicholas D. Lucchesi
*Attorney, Agent, or Firm*—Woodard, Emhardt, Naughton, Moriarty & McNett

[57] ABSTRACT

A dental mirror apparatus for use by a dentist to observe portions of the oral cavity obstructed from direct view comprises a mirror attached to the distal end of a stem. The proximal end of the stem is connected to a clip or ring for engaging the dentist's finger to permit finger manipulation of the mirror in the patient's mouth. The dental apparatus may include a telescoping stem and various joint configurations to permit adjustment of the position of the mirror relative to the dentist's finger or the proximal end of the stem. In one embodiment, a light source is attached thereto to assist in viewing of the oral cavity.

8 Claims, 4 Drawing Sheets

5,458,486

DENTAL MIRROR APPARATUS

REFERENCE TO RELATED APPLICATIONS

This is a continuation-in-part application of prior application Ser. No. 07/852,966, filed on Mar. 17, 1992, of Stephen L. Ballard now abandoned.

BACKGROUND OF THE INVENTION

This invention relates to dental mirrors which are positionable within a patient's mouth and particularly to a novel mirror apparatus which permits easy manipulation of the mirror for viewing in the oral cavity.

A dentist often must observe areas of the oral cavity which are obstructed from direct view in the course of his practice. Dentists commonly use mirrors mounted on a long handheld stem to observe those hidden areas. These hand held mirrors require the use of one of the dentist's hands for grasping and the manipulation of the mirror, leaving only one free hand to perform the dental procedures. In addition, the mirror itself, and more particularly the support stem, can become an impediment or obstruction during the dental procedure. The present invention addresses these and other problems associated with current dental mirrors.

SUMMARY OF THE INVENTION

The invention contemplates a dental mirror apparatus which is positionable within a patient's mouth by a dentist. The apparatus includes a mirror, a stem having a proximal end and a distal end, means for attaching the mirror to the distal end, and means at the proximal end of the stem for engaging the stem to and supporting the stem on a finger of the dentist to permit finger manipulation of the mirror in the patient's mouth. The means for engaging the finger may include a curved retainer clip or ring sized to fit the dentist's finger. The clip or ring may be adjustable.

One embodiment of the dental mirror apparatus includes means for adjusting the position of the mirror relative to the proximal end of the stem or relative to the means for engaging the finger. This feature allows adjustment of the configuration of the apparatus to permit viewing of less accessible areas of the oral cavity.

Another embodiment of the dental mirror apparatus includes a stem having telescoping means for varying the length of the stem and consequently the distance that the mirror projects from the dentist's finger. This telescoping feature also increases the ease and flexibility of use of the apparatus.

The dental mirror apparatus may also include a light source attached to the mirror portion to aid the dentist in viewing the oral cavity. The light source may comprise a ring light around the circumference of the mirror to provide shadowless illumination of the oral cavity or a point light source.

Yet another embodiment of the dental mirror apparatus omits the stem. This embodiment includes a mirror, a means for engaging the finger, and a means for attaching the mirror to the means for engaging the finger. The means for attachment may fix or allow variance of the mirror's angular position with the dentist's finger.

One object of the present invention is to provide a dental mirror apparatus that engages the dentist's finger to facilitate observation of portions of the oral cavity that are obstructed from direct view with enhanced efficiency and minimal loss of hand and finger dexterity.

Another object of the present invention is to provide a dental mirror apparatus which includes means for adjusting the mirror position to aid in viewing areas of the oral cavity that are obstructed from view. A further object of the present invention is to provide a dental mirror apparatus having a light source attached thereto that provides illumination of the area to be viewed.

Another object of the present invention is to simplify dental procedures for dentists by providing an improved method of observing the oral cavity that frees both of the dentist's hands for tasks other than grasping a mirror.

Other objects, and certain benefits, of the present invention will become apparent to those of ordinary skill in the art from the following written description and accompanying figures.

DESCRIPTION OF THE PREFERRED EMBODIMENTS

Figure 1:
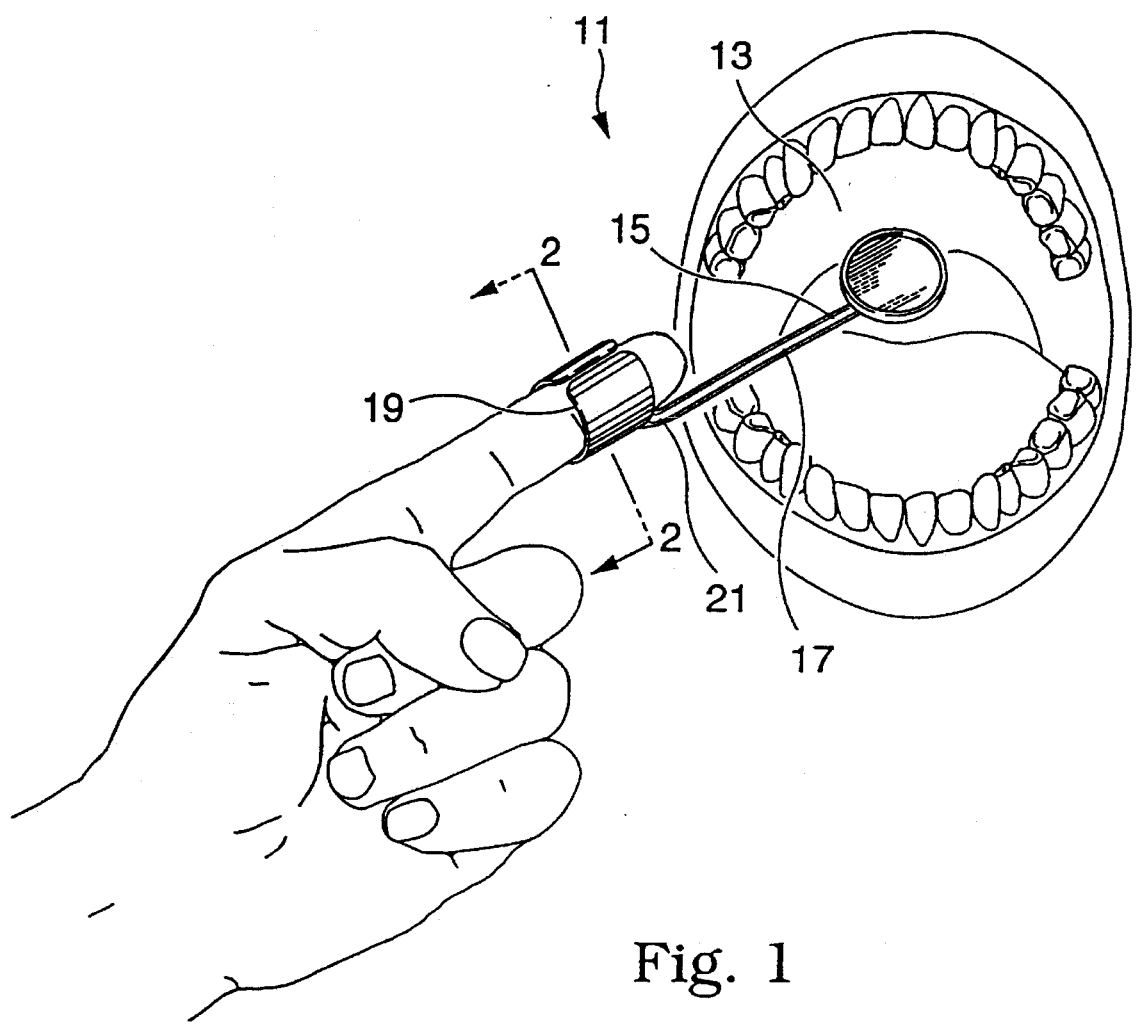
FIG. 1 is a perspective view of a dental finger mirror having a curved clip to fit over and engage the finger as means for engaging the finger. The dental mirror apparatus is shown placed in a patient's mouth for observing portions thereof.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
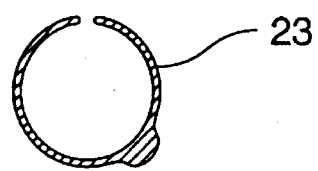
FIG. 2 is a cross section of dental finger mirror in FIG. 1.
Figure 3:
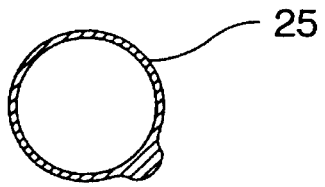
FIG. 3 is a cross sectional view of an alternative embodiment of the means for engaging of FIG. 1.

Referring to FIGS. 1, 2 and 3, a dental mirror apparatus 11 is illustrated which can be placed in a patient's mouth. The dental mirror apparatus 11 includes a mirror 13 that is attached to the distal end 15 of a stem 17. The dental mirror apparatus also includes means for engaging 19 the proximal end 21 of the stem to and supporting the stem on a dentist's finger to permit finger manipulation of the mirror in and around the patient's mouth.

Referring to FIGS. 2 and 3, cross sectional views of means for engaging 19 are shown. FIG. 2 illustrates one embodiment of the means for engaging 19 which is a curved clip 23. The clip may be rigid or bendable depending on the flexibility of the material used. A rigid clip sized to fit over and engage the dentist's finger may be slid over the finger tip. Alternatively, a bendable clip allows engagement of the apparatus to fingers of different sizes by allowing a gap between the clip arms to be pulled apart for use with larger fingers or pushed together for use with smaller fingers.

FIG. 3 illustrates an alternative embodiment of the means for engaging 19 which comprises a ring 25 sized to slip over a dentist's finger. Other means for engaging the finger are also contemplated which may be adjustable for ring size, such as an adjustable ring having a sliding rigid band or a ring having a flexible strap which may adjustably engage the finger. The flexible strap may include a buckle or hook and loop type fastener for adjustment to different finger sizes.

The dentist can use the apparatus 11 by slipping the means for engaging 19 over his finger. The position of the mirror may be adjusted by moving the finger supporting the apparatus 11 within the oral cavity to facilitate viewing. The remaining fingers on the supporting hand are free to be used in performing a variety of dental tasks while the apparatus is used. The dental mirror will typically be placed on a finger of the non-dominant hand, leaving the dominant hand to perform other operations requiring greater dexterity.

Alternative embodiments of the dental finger mirror are contemplated which include means for adjusting the position of the mirror 13 relative the means for engaging 19. The adjustment feature offers increased flexibility for observing portions of the oral cavity which are obstructed from direct view because the configuration of the finger mirror can be altered. The mirror angle can be adjusted by the dentist and the stem may be rotated or swiveled to provide for easier viewing of areas of the oral cavity which may be difficult to access.

Figure 4:
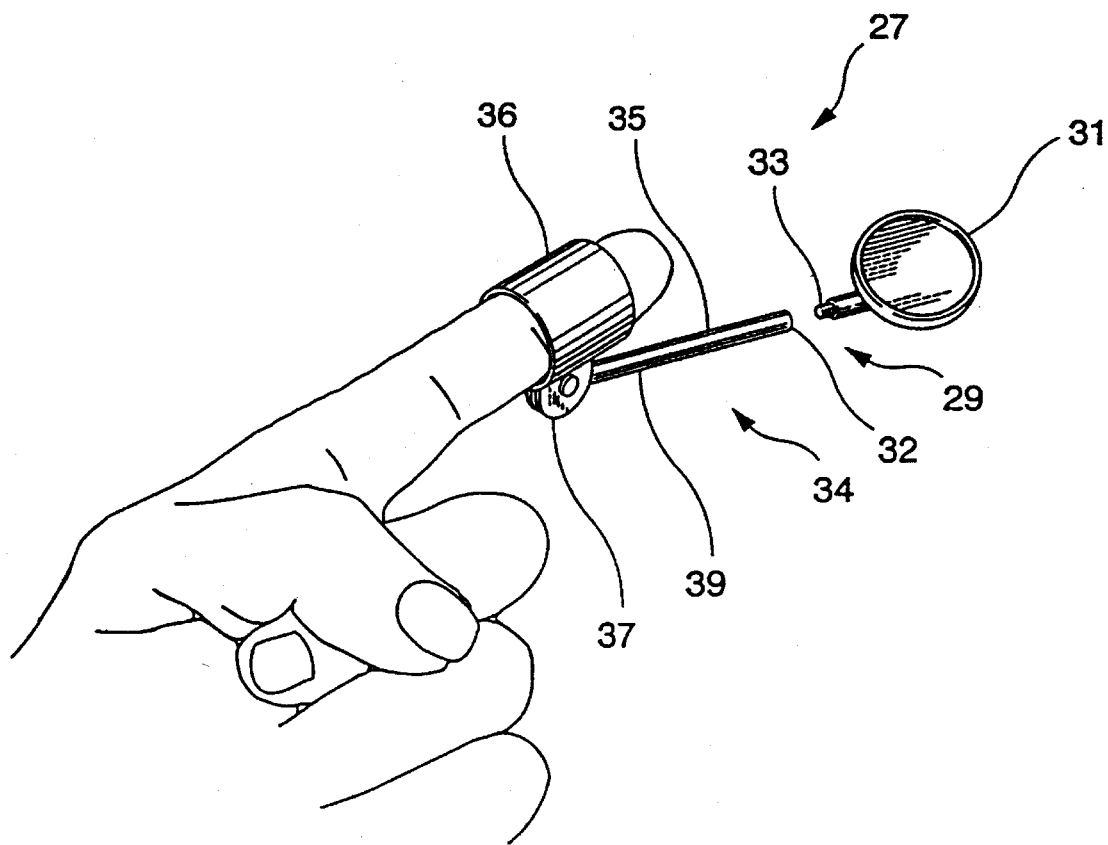
FIG. 4 is a perspective view of a dental mirror including a presized ring as means for engaging the finger. The dental mirror apparatus includes a pivot which connects the stem to the means for engaging the finger and a typical removable dental mirror.

Referring to FIG. 4, an alternative embodiment of the dental mirror apparatus is shown. The dental mirror apparatus 27 includes the elements of the dental mirror apparatus 11 illustrated in FIG. 1. The apparatus additionally includes means 29 for removably mounting a standard dental mirror 31 to the distal end 32 by use of a male threaded portion 33 on the mirror and complementary threaded female portion (not shown) on the distal end. In FIG. 4, the mirror 31 is shown prior to mounting to the apparatus.

This embodiment also includes means 34 for adjusting the position of the mirror 31, which is attached to the stem 35, relative to the means for engaging 36. The means for adjusting 34 includes a pivot 37 which allows 180 degree movement along a single plane and which connects the means for engaging 36 to the proximal end 39 of the stem.

It is contemplated that the dental mirror apparatus of the present invention include means for mounting a standard dental mirror which is complementary to the mounting means on the standard mirror. The additional capability offered by releasably mounting standard mirrors may allow the dentist to select mirrors of different sizes or mirrors that magnify the viewing area.

Figure 8:
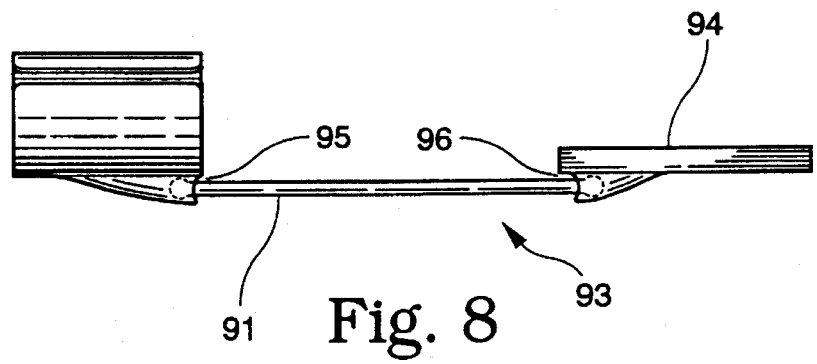
FIG. 8 is a side view of the dental mirror apparatus which includes a ball and socket joint on both ends of the stem.

Referring to FIG. 8, a side view of a dental mirror apparatus 90 is illustrated. The dental mirror apparatus includes the elements of the dental mirror apparatus 11 illustrated in FIG. 1 such as a stem 91 and a means for engaging the finger 92. In alternative embodiments, the means 93 for adjusting the position of the mirror 94, relative to the means for engaging 92, may comprise ball and socket joints, 95 and 96, respectively at either or both ends of stem 91. The ball and socket joints provide a greater range of adjustment than the pivot 37 illustrated in FIG. 4.

Figure 5:
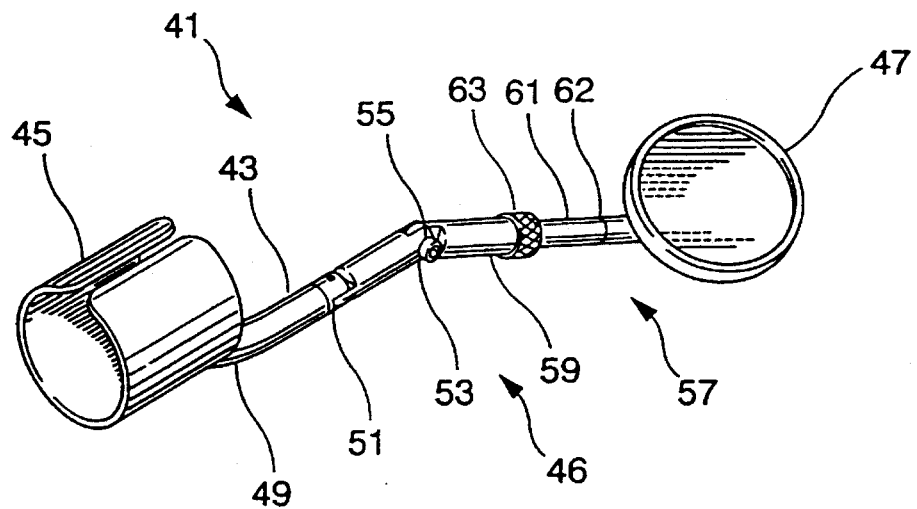
FIG. 5 is a perspective view of the dental mirror apparatus having a curved clip for engaging the finger and having means for adjusting the position of the mirror relative to the proximal end which includes an offset pair of pivots. Telescoping means are also shown.

Referring to FIG. 5, a perspective view of a dental mirror apparatus 41 is illustrated. The dental mirror apparatus includes the elements of the dental mirror apparatus 11 illustrated in FIG. 1 such as a stem 43 and means for engaging the finger 45. Additionally, the apparatus 41 includes means 46 for adjusting the position of the mirror 47 relative to the proximal end 49. The means for adjusting 46 include a proximal pivot 51 and a distal pivot 53. Each pivot provides 180 degree movement along a single plane. The pivot planes of the pivots 51 and 53 are offset 90 degrees from each other to allow mirror adjustment in two different planes. The dentist may adjust the mirror position relative to the proximal end by adjusting the angle of one or both of the pivots prior to or during use of the apparatus.

It is also contemplated that pivot tension be adjusted by using an Allen wrench to tighten or loosen the Allen head screws 55 used attach the pivot sections. The dentist may also lock the pivots in a desired orientation by tightening the screws. The use of rivets as an alternative to Allen screws for attachment of the pivots is also contemplated providing the pivots have sufficient frictional resistance to hold a given angle.

The dental mirror apparatus 41 also includes telescoping means 57 for mounting the mirror 47 to the distal end of a hollow stem 59. The telescoping means 57 includes a mirror shaft 61 which is slidably disposed within the hollow stem 59 and which is secured in its desired position by a locking collet 63. The telescoping means also permits rotation of the mirror 360 degrees about the stem axis by rotating the shaft relative to the distal end and by locking the collet when the desired position is reached. In alternative embodiments the telescoping and rotating degrees of freedom can be combined or provided singly. The mirror 47 is a standard dental mirror and is shown mounted to the mirror shaft 61 by mounting means 62, (such as shown in FIG. 4).

Figure 6:
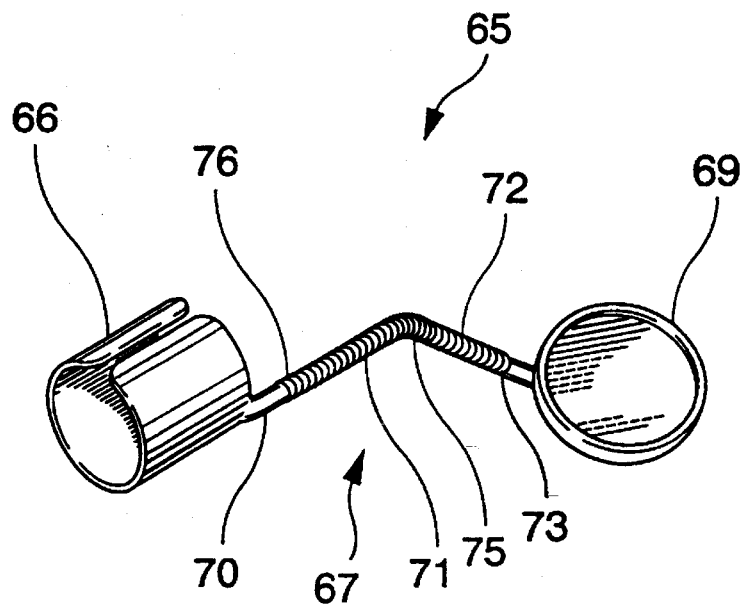
FIG. 6 is a perspective view of the dental mirror apparatus of FIG. 1 which includes a bendable stem that is bent to adjust the position of the mirror relative to the proximal end.

FIG. 6 is a perspective view of a dental mirror apparatus 65 which includes the elements of dental mirror apparatus 11 illustrated in FIG. 1 including a means for engaging 66. The apparatus 65 also includes means 67 for adjusting the position of the mirror 69 relative to the proximal end 70. In this embodiment, the means for adjusting includes a bendable stem 71. The stem 71 can be of a spring sheath construction so that the stem can be bent anywhere along its length. The mirror 69 is shown mounted to the distal end 72 by mounting means 73, (such as shown in FIG. 4). The stem 71 is shown with a bend 75 which alters the orientation of the mirror relative to the proximal end 70 of the stem. The stem 71 is attached at the proximal end 70 by means for attachment 76 to allow the stem 71 to be replaced because bending may shorten the life of the stem compared to other portions of the device.

Figure 7:
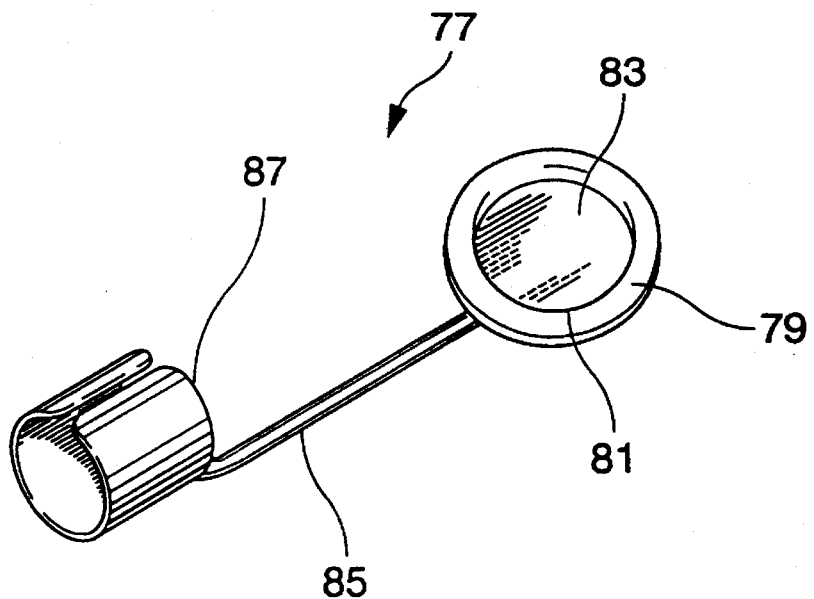
FIG. 7 is a perspective view of the dental mirror apparatus which includes a ring light source to aid in viewing the oral cavity.

Referring to FIG. 7, an alternative embodiment of the dental mirror apparatus 77 is shown which includes a light source. The dental mirror apparatus 77 includes the elements of the dental mirror apparatus 11 illustrated in FIG. 1 with the addition of a ring light 79 placed around the circumference 81 of the mirror 83. The dental mirror apparatus 77 also includes a stem 85, and means 87 for engaging the dentist's finger. It is contemplated that the dental mirror apparatus 77 include a variety of means for engaging the finger and means for adjusting the mirror position. Embodiments of dental mirror apparatus having a light source are especially useful because the light source provides illumination to more easily observe portions of the oral cavity. The light source may be a ring light as shown in FIG. 7 placed around the circumference of the mirror or alternatively may be a point light source. One advantage of a ring light is its ability to decrease shadows by producing an even, diffuse light. The light source may be powered by a small battery located in the device or a cord may be utilized to provide power from an alternative source such as a finger supported battery. Fiber optics may also be used to convey the light into the oral cavity.

Figure 9:
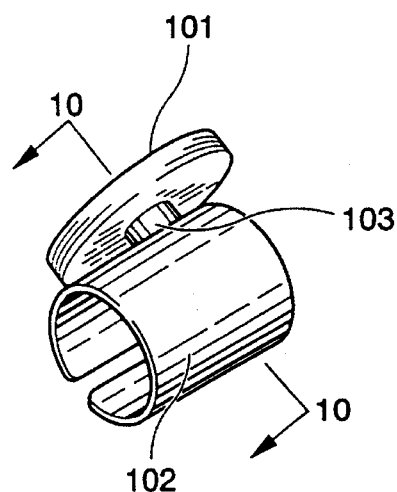
FIG. 9 is a perspective view of a further embodiment dental mirror apparatus which allows the mirror to reside in close proximity to the engaging finger.
Figures 10, 11:
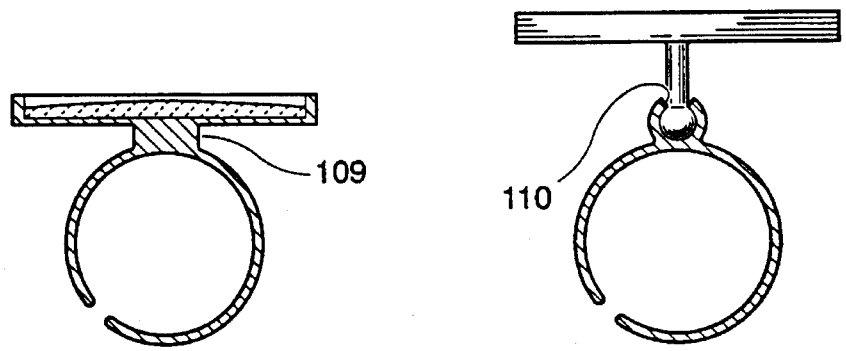
FIG. 10 is a cross section of dental mirror apparatus of FIG. 9.
FIG. 11 is a cross sectional view of an alternative embodiment of the means for attaching the mirror to the finger clip of FIG. 9.

Referring to FIGS. 9, 10 and 11, a further embodiment of a dental mirror apparatus 100 is illustrated which can be placed in a patient's mouth. The dental mirror apparatus 100 includes a mirror 101 that is attached in close proximity to the dentist's finger. The mirror apparatus includes the means 102 for engaging a dentist's finger to permit finger manipulation of the mirror in and around the patient's mouth. In the preferred embodiment, this means for engaging 102 is a clip similar to clip 23 described above. Alternatively, the means 102 can be a ring, such as ring 25 (FIG. 3), or other suitable means for tightly encircling the dentist's fingers.

The mirror 101 is connected to the clip 102 by way of means for attachment 103. Referring to FIGS. 10 and 11, cross sectional views of means for attachment 103 are shown. FIG. 10 illustrates one embodiment of the means for attachment 103 which is a rigid connection 109. FIG. 11 illustrates an alternative embodiment in which the means for attachment 103 is a movable connection such as a ball and socket joint 110. In this embodiment, the stem on the ball of the joint must be short to keep the mirror in close proximity to the dentist's finger, preferably no longer than 1 centimeter.

Apparatus 100 of FIG. 9 offers several benefits when used. Apparatus 100 requires less overall space in the limited area available in and around a patient's mouth because the mirror 101 is retained in close proximity to the dentist's finger. The mirror is placed inside and manipulated within the patients mouth directly with the dentist's finger. In this manner, adjacent fingers on the dentist's same hand are available for use to manipulate other tools inside the patient's mouth that the dentist might be using at the same time as the mirror. A further operational benefit is that less likelihood exists the mirror will be inadvertently moved from the focused position during use. The mirror is comparatively less exposed to the movements of a patent's mouth or other dental instruments because the mirror is located in close proximity to the dentist's finger and is somewhat shielded by the dentist's fingers. Yet, if the focal point is lost because the mirror is inadvertently bumped from the proper plane of operation, fingers adjacent the finger engaging the mirror can be used to move the mirror back into the proper plane.

It is contemplated that the dental mirror apparatus described above can be formed mainly of stainless steel to permit the apparatus to be sterilized before reuse.

Several benefits and advantages of the present invention over prior dental mirrors include adjustment of the mirror angle by simple manipulation of the finger to which it is engaged. An additional advantage is the ability to utilize both hands for performing dental procedures when using the dental finger mirror rather than the restriction of having only one free hand because the second hand is required to grasp the dental mirror.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A dental mirror apparatus for use by a dentist, the apparatus being positionable within a patient's mouth comprising:

a mirror;

a stem having a proximal end and a distal end wherein said stem includes telescoping means for varying the length of said stem;

a locking collet for fixing said telescoping means in an extended position;

means for attaching said mirror to said distal end of said stem; and means at said proximal end of said stem for engaging said stem to and supporting said stem on a finger of the dentist to permit finger manipulation of the mirror in the patient's mouth.

2. The apparatus of claim 1 wherein said means for engaging includes a ring having an internal diameter sized to retain said apparatus on the dentist's finger.

3. The apparatus of claim 1 wherein said means for engaging includes a resilient curved retainer clip to resiliently clamp onto the dentist's finger.

4. The apparatus of claim 1 wherein said means for engaging is adjustable for engaging fingers of different sizes.

5. The apparatus of claim 4 wherein said means for engaging includes a ring having an adjustable inner diameter.

6. The apparatus of claim 1 further comprising a light source attached to said mirror.

7. The apparatus of claim 6 wherein said mirror includes a circumference and said light source forms a ring around said circumference.

8. A dental apparatus for use by a dentist, the apparatus being positionable within a patient's mouth comprising:

a mirror;

a hollow stem having a proximal end and a distal end;

means for attaching said mirror to said distal end of said stem, said means for attaching including a mirror shaft attached to said mirror and slidably disposed within said hollow stem;

means at said proximal end of said stem for engaging said stem to and supporting said stem on a finger of the dentist to permit finger manipulation of the mirror in the patient's mouth;

means for adjusting the position of the mirror relative to said proximal end wherein said means for adjusting is located at said proximal end; and telescoping means for varying the length of said stem, said telescoping means including:

a locking collet to secure said shaft inside said stem.

* * * * *